(12) United States Patent
Beaupré

(10) Patent No.: US 7,479,148 B2
(45) Date of Patent: Jan. 20, 2009

(54) ULTRASONIC SHEAR WITH ASYMMETRICAL MOTION

(75) Inventor: Jean Beaupré, Cincinnati, OH (US)

(73) Assignee: Crescendo Technologies, LLC, Cincinnati, OH (US)

( * ) Notice: Subject to any disclaimer, the term of this patent is extended or adjusted under 35 U.S.C. 154(b) by 422 days.

(21) Appl. No.: 11/261,243

(22) Filed: Oct. 28, 2005

(65) Prior Publication Data

US 2006/0100652 A1    May 11, 2006

Related U.S. Application Data

(60) Provisional application No. 60/625,885, filed on Nov. 8, 2004.

(51) Int. Cl.
*A61B 17/32* (2006.01)
(52) U.S. Cl. ...................................... 606/169
(58) Field of Classification Search ........................ None
See application file for complete search history.

(56) References Cited

U.S. PATENT DOCUMENTS

| | | |
|---|---|---|
| 2,990,616 A | 7/1961 | Balamuth et al. |
| 3,053,124 A | 9/1962 | Balamuth et al. |
| 3,086,288 A | 4/1963 | Balamuth et al. |
| 3,526,219 A | 9/1970 | Balamuth et al. |
| 3,636,943 A | 1/1972 | Balamuth et al. |
| 3,830,240 A | 8/1974 | Antonevich et al. |
| 3,861,391 A | 1/1975 | Antonevich et al. |
| 3,862,630 A | 1/1975 | Balamuth |
| 3,990,452 A | 11/1976 | Murry et al. |
| 4,136,700 A | 1/1979 | Broadwin et al. |
| 4,169,984 A | 10/1979 | Parisi |
| 4,526,571 A | 7/1985 | Wuchinich |
| 4,634,419 A | 1/1987 | Kreizman et al. |
| 4,724,351 A | 2/1988 | EerNisse et al. |
| 4,911,161 A | 3/1990 | Schechter |
| 4,920,954 A | 5/1990 | Alliger et al. |
| 4,974,581 A | 12/1990 | Wiksell |
| 4,992,048 A | 2/1991 | Goof |
| 5,019,083 A | 5/1991 | Klapper et al. |

(Continued)

FOREIGN PATENT DOCUMENTS

DE    203229    10/1983

(Continued)

*Primary Examiner*—Kevin T Truong
(74) *Attorney, Agent, or Firm*—Greenebaum Doll & McDonald PLLC; Glenn D. Bellamy

(57) ABSTRACT

Devices providing ultrasonic clamped cutting using asymmetrical motion include a housing and ultrasonic waveguide. A longitudinal axis extends through the center of mass of the ultrasonic waveguide. An actuating assembly provides opposable movement of a clamp arm with respect to the cutting blade, the movement defining a vertical plane having a vertical axis orthogonal to both the longitudinal axis and a horizontal axis. An end-effector coupled to the ultrasonic waveguide includes a cutting blade that cuts using ultrasonic motion. The blade's center of mass may be offset from the longitudinal axis, providing motion of the blade in both the longitudinal and vertical axes concurrently. Excursion of the cutting blade in the direction of the horizontal axis that may be limited to less than 92%, and in the direction of the vertical axis of more than 8%, of an excursion of the cutting blade in the direction of the longitudinal axis.

20 Claims, 8 Drawing Sheets

U.S. PATENT DOCUMENTS

| | | | |
|---|---|---|---|
| 5,047,008 A | 9/1991 | de Juan, Jr. et al. | |
| 5,047,043 A | 9/1991 | Kubota et al. | |
| 5,180,363 A | 1/1993 | Idemoto et al. | |
| 5,188,102 A | 2/1993 | Idemoto et al. | |
| 5,205,817 A | 4/1993 | Idemoto et al. | |
| 5,221,282 A | 6/1993 | Wuchinich | |
| 5,222,937 A | 6/1993 | Kagawa | |
| 5,248,296 A | 9/1993 | Alliger | |
| 5,263,957 A | 11/1993 | Davison | |
| 5,312,329 A | 5/1994 | Beaty et al. | |
| 5,318,570 A | 6/1994 | Hood et al. | |
| 5,322,055 A | 6/1994 | Davison et al. | |
| 5,397,293 A | 3/1995 | Alliger et al. | |
| 5,413,578 A | 5/1995 | Zahedi | |
| 5,417,654 A | 5/1995 | Kelman | |
| 5,480,379 A | 1/1996 | La Rosa | |
| 5,531,597 A | 7/1996 | Foulkes et al. | |
| 5,653,724 A | 8/1997 | Imonti | |
| 5,669,922 A | 9/1997 | Hood | |
| 5,676,649 A | 10/1997 | Boukhny et al. | |
| 5,893,835 A * | 4/1999 | Witt et al. | 601/2 |
| 6,024,750 A | 2/2000 | Mastri et al. | |
| 6,129,735 A * | 10/2000 | Okada et al. | 606/169 |
| 6,283,981 B1 | 9/2001 | Beaupre | |
| 6,309,400 B2 | 10/2001 | Beaupre | |
| 6,325,811 B1 | 12/2001 | Messerly | |
| 6,328,751 B1 | 12/2001 | Beaupre | |
| 6,432,118 B1 | 8/2002 | Messerly | |
| 6,436,115 B1 | 8/2002 | Beaupre | |
| 6,491,708 B2 | 12/2002 | Madan et al. | |
| 6,660,017 B2 * | 12/2003 | Beaupre | 606/169 |
| 6,752,815 B2 | 6/2004 | Beaupre | |
| 6,773,444 B2 | 8/2004 | Messerly | |
| 6,969,439 B1 | 11/2005 | Takagi | |
| 6,976,969 B2 | 12/2005 | Messerly | |
| 2005/0234484 A1 | 10/2005 | Houser et al. | |

FOREIGN PATENT DOCUMENTS

| | | |
|---|---|---|
| EP | 0456470 A1 | 11/1991 |
| EP | 0830845 A1 | 3/1998 |
| GD | 203229 | 1/1982 |
| WO | WO86/02257 | 4/1986 |
| WO | WO93/14709 | 8/1993 |

* cited by examiner ical Patent
ULTRASONIC SHEAR WITH ASYMMETRICAL MOTION

This application claims the benefit of Provisional Patent Application Ser. No. 60/625,885, filed on Nov. 8, 2004, to which priority is claimed pursuant to 35 U.S.C. §119(e) and which is hereby incorporated herein by reference.

BACKGROUND OF THE INVENTION (a) Field of the Invention

The present invention relates, in general, to ultrasonic devices and, more particularly, to methods and devices that provide ultrasonic clamped cutting using asymmetrical motion.

(b) Description of the Prior Art

The fields of ultrasonics and stress wave propagation encompass applications ranging from non-destructive testing in materials science, to beer packaging in high-volume manufacturing. Diagnostic ultrasound uses low-intensity energy in the 0.1-to-20-MHz region to determine pathological conditions or states by imaging. Therapeutic ultrasound produces a desired bio-effect, and can be divided further into two regimes, one in the region of 20 kHz to 200 kHz, sometimes called low-frequency ultrasound, and the other in the region from 0.2 to 10 MHz, where the wavelengths are relatively small, so focused ultrasound can be used for therapy. At high intensities of energy, this application is referred to as HIFU for High Intensity Focused Ultrasound.

Examples of therapeutic ultrasound applications include HIFU for tumor ablation and lithotripsy, phacoemulsification, thrombolysis, liposuction, neural surgery and the use of ultrasonic scalpels for cutting and coagulation. In low-frequency ultrasound, direct contact of an ultrasonically active end-effector or surgical instrument delivers ultrasonic energy to tissue, creating bio-effects. Specifically, the instrument produces heat to coagulate and cut tissue, and cavitation to help dissect tissue planes. Other bio-effects include: ablation, accelerated bone healing and increased skin permeability for transdermal drug delivery.

Ultrasonic medical devices are used for the safe and effective treatment of many medical conditions. Ultrasonic surgical instruments are advantageous because they may be used to cut and/or coagulate organic tissue using energy, in the form of mechanical vibrations, transmitted to a surgical end-effector at ultrasonic frequencies. Ultrasonic vibrations, when transmitted to organic tissue at suitable energy levels and using a suitable end-effector, may be used to cut, dissect, or cauterize tissue.

Ultrasonic vibration is induced in the surgical end-effector by, for example, electrically exciting a transducer which may be constructed of one or more piezoelectric or magnetostrictive elements in the instrument hand piece. Vibrations generated by the transducer section are transmitted to the surgical end-effector via an ultrasonic waveguide extending from the transducer section to the surgical end-effector. The waveguide/end-effector combinations are typically designed to resonate at the same frequency as the transducer. Therefore, when an end-effector is attached to a transducer the overall system frequency is still the same frequency as the transducer itself.

At the tip of the end-effector, ultrasonic energy is delivered to tissue to produce several effects. Effects include the basic gross conversion of mechanical energy to both frictional heat at the blade-tissue interface, and bulk heating due to viscoelastic losses within the tissue. In addition, there may be the ultrasonically induced mechanical mechanisms of cavitation, microstreaming, jet formation, and other mechanisms.

Ultrasonic surgical instruments utilizing solid core technology are particularly advantageous because of the amount of ultrasonic energy that may be transmitted from the ultrasonic transducer through a solid waveguide to the active portion of the end-effector, typically designated as a blade. Such instruments are particularly suited for use in minimally invasive procedures, such as endoscopic or laparoscopic procedures, wherein the end-effector is passed through a trocar to reach the surgical site.

Solid core ultrasonic surgical instruments may be divided into two types, single element end-effector devices and multiple-element end-effector. Single element end-effector devices include instruments such as scalpels, and ball coagulators, see, for example, U.S. Pat. No. 5,263,957. While such instruments as disclosed in U.S. Pat. No. 5,263,957 have been found eminently satisfactory, there are limitations with respect to their use, as well as the use of other ultrasonic surgical instruments. For example, single-element end-effector instruments have limited ability to apply blade-to-tissue pressure when the tissue is soft and loosely supported. Substantial pressure is necessary to effectively couple ultrasonic energy to the tissue. This inability to grasp the tissue results in a further inability to fully coapt tissue surfaces while applying ultrasonic energy, leading to less-than-desired hemostasis and tissue joining.

A multiple element end-effector including a clamp mechanism in an ultrasonic surgical device has been described in U.S. Pat. Nos. 3,636,943 and 3,862,630 to Balamuth. Generally, however, the Balamuth device, as disclosed in those patents, may not coagulate and cut sufficiently fast, and may lack versatility in that it cannot be used to cut/coagulate without the clamp because access to the blade is blocked by the clamp.

Multiple element end-effectors include those illustrated in devices such as ultrasonic shears, for example, those disclosed in U.S. Pat. Nos. 5,322,055 and 5,893,835 provide an improved ultrasonic surgical instrument for cutting/coagulating tissue, particularly loose and unsupported tissue. The ultrasonic blade in a multiple-element end-effector is employed in conjunction with a clamp for applying a compressive or biasing force to the tissue. Clamping the tissue against the blade provides faster and better controlled coagulation and cutting of the tissue.

Although ultrasonic shears such as, those disclosed in U.S. Pat. Nos. 5,322,055 and 5,893,835 have been found satisfactory, there may be limitations with respect to their use. For example, the devices disclosed in U.S. Pat. Nos. 5,322,055 and 5,893,835 operate primarily in a longitudinal mode of vibration. End-effectors of devices that operate in primarily longitudinal mode exhibit a sinusoidally diminishing effectiveness proximally from the distal end of the end-effector. As the longitudinal excursion diminishes, the effectiveness of the end-effector diminishes. This currently limits the effective length of ultrasonic devices to a fraction of their wavelength, usually substantially less that ¼ wavelength, to stay away from the node at ¼ wavelength.

SUMMARY OF THE INVENTION

The present invention is directed to methods and devices that provide ultrasonic clamped cutting using asymmetrical motion. An ultrasonic clamping device in accordance with embodiments of the present invention may include a housing with an elongated support member having a proximal end joined to the housing, and a distal end. In one embodiment, the elongated support member defines a longitudinal axis. An ultrasonic waveguide may be positioned within the elongated support member, wherein the longitudinal axis extends through the center of mass of the ultrasonic waveguide. An actuating assembly is coupled to the housing, the actuating assembly including an actuator and a reciprocal member at least partially positioned within the elongated support member. The reciprocal member is operatively connected to the actuator. An end-effector extends distally from the distal end of the elongated support member. The end-effector includes a cutting blade configured to cut using ultrasonic motion, the cutting blade coupled to the ultrasonic waveguide. The center of mass of the cutting blade is offset from the longitudinal axis, thereby providing motion of the cutting blade in both the longitudinal and vertical axes concurrently. A clamp arm is coupled to the distal end of the elongated support member and configured for opposable movement with respect to the cutting blade, the opposable movement defining a vertical plane. The vertical plane is defined as having a vertical axis orthogonal to both the longitudinal axis and a horizontal axis, where the clamp arm is operatively connected to the reciprocal member so that reciprocal movement of the reciprocal member opposes the clamp arm with the cutting blade.

Further embodiments of devices in accordance with the present invention provide an excursion of the cutting blade in the direction of the horizontal axis that is limited to less than about 92%. Other embodiments of devices in accordance with the present invention provide for an excursion of the cutting blade in the direction of the vertical axis of more than about 8% of an excursion of the cutting blade in the direction of the longitudinal axis. Embodiments of devices in accordance with the present invention provide an excursion of the cutting blade in the direction of the horizontal axis that is more than about 8% of an excursion of the cutting blade in the direction of the longitudinal axis. Still further embodiments of devices in accordance with the present invention provide an excursion of the cutting blade in the direction of the vertical axis and the horizontal axis of more than about 8% of an excursion of the cutting blade in the direction of the longitudinal axis.

The cutting blade may be symmetrical with respect to the vertical plane, and may further be circularly symmetric about a blade axis extending through the center of mass of the cutting blade. In another embodiment the cutting blade is circularly symmetric about a blade axis extending through the center of mass of the cutting blade, wherein the blade axis is parallel to the longitudinal axis.

The cutting blade may have a colored coating. The cutting blade may be configured for surgical cutting of tissue. The entire device may be sterilized and provided in a sterility preserving container.

In another embodiment of a device in accordance with the present invention, an ultrasonic clamping device includes a housing having an ultrasonic waveguide coupled to the housing. The ultrasonic waveguide has a longitudinal axis extending through its center of mass. An actuating assembly is coupled to the housing, the actuating assembly including an actuator and a reciprocal member operatively connected to the actuator. In one embodiment, an end-effector extends distally from the housing, the end-effector including a cutting blade configured to cut using ultrasonic motion. The cutting blade may be coupled to the ultrasonic waveguide. A clamp arm is configured for opposable movement with respect to the cutting blade, the opposable movement defining a vertical plane, the vertical plane having a vertical axis orthogonal to both the longitudinal axis and a horizontal axis. The clamp arm is operatively connected to the reciprocal member so that reciprocal movement of the reciprocal member clamps the clamp arm with respect to the cutting blade. The center of mass of the cutting blade may be offset from the longitudinal axis, thereby providing motion of the cutting blade in both the longitudinal and vertical axis directions concurrently.

In still a further embodiment of a device in accordance with the present invention, an ultrasonic clamping device includes a housing having an ultrasonic waveguide coupled to the housing. The ultrasonic waveguide has a longitudinal axis extending through its center of mass. An actuating assembly is coupled to the housing, the actuating assembly including an actuator and a reciprocal member operatively connected to the actuator. An end-effector extends distally from the housing, the end-effector including a cutting blade configured to cut using ultrasonic motion. A clamp arm is configured for opposable movement with respect to the cutting blade, the opposable movement defining a vertical plane, the vertical plane having a vertical axis orthogonal to both the longitudinal axis and a horizontal axis. The clamp arm is operatively connected to the reciprocal member so that reciprocal movement of the reciprocal member clamps the clamp arm with respect to the cutting blade. The cutting blade is coupled to the ultrasonic waveguide, wherein the longitudinal axis extends through the center of mass of the cutting blade. The proximal end of the cutting blade includes an asymmetry configured to convert longitudinal motion of the waveguide into motion of the cutting blade in both the longitudinal and vertical axis directions concurrently.

A further embodiment of a device in accordance with the present invention includes an ultrasonic waveguide having a longitudinal axis extending through the center of mass of the ultrasonic waveguide. A cutting blade is configured to cut using ultrasonic motion, the cutting blade coupled to the ultrasonic waveguide, wherein the center of mass of the cutting blade is offset from the longitudinal axis, thereby converting at least a portion of the longitudinal motion of the ultrasonic waveguide into motion of the cutting blade normal to the longitudinal axis.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

BRIEF DESCRIPTION OF THE DRAWINGS

The features of the invention may be set forth with particularity in the appended claims. The invention itself, however, both as to organization and methods of operation, together with further objects and advantages thereof, may best be understood by reference to the following description, taken in conjunction with the accompanying figures of the drawing in which:

Figure 1:
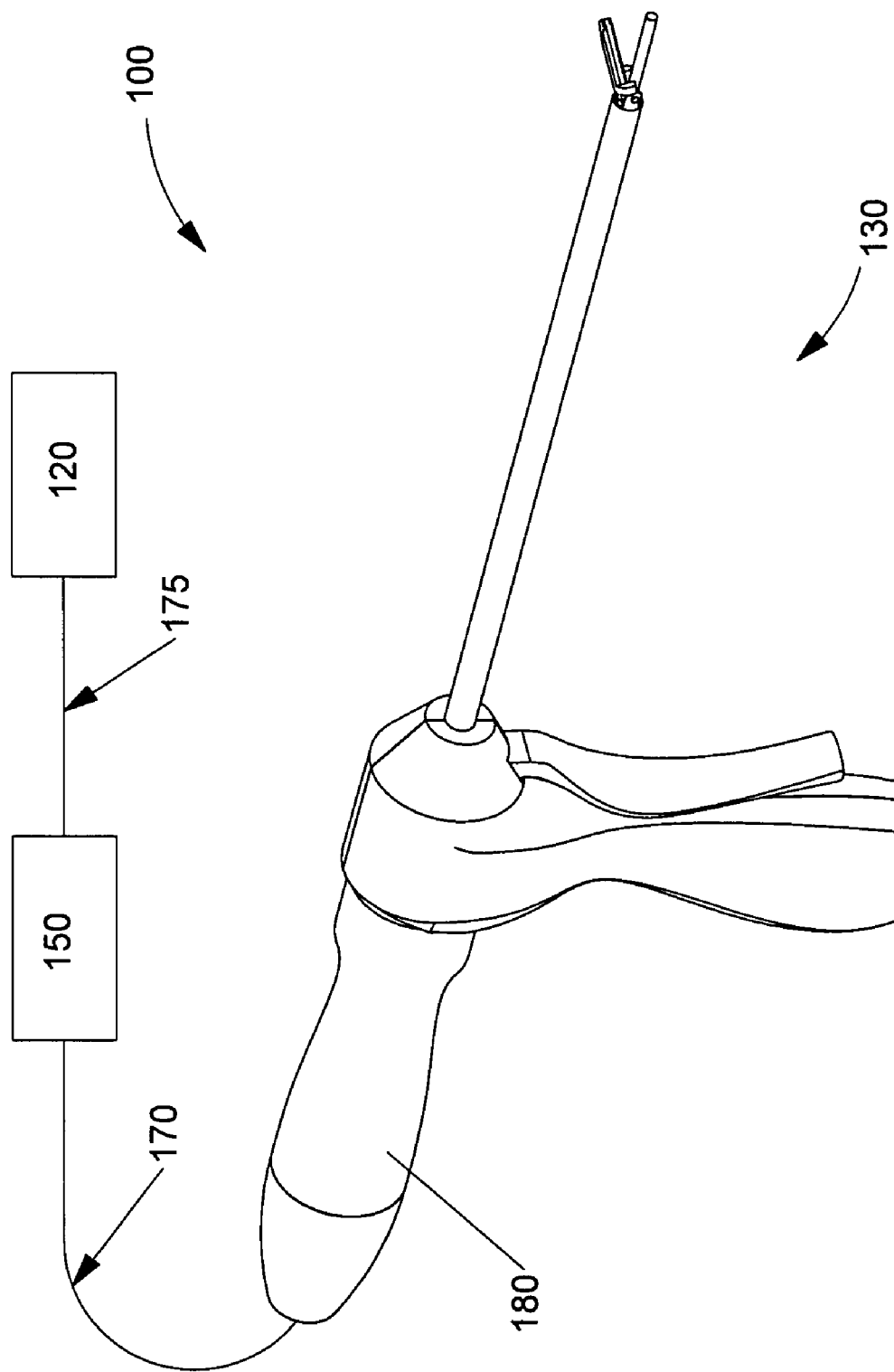
FIG. 1 is a perspective view of an ultrasonic shear system in accordance with embodiments of the present invention.

While the invention is amenable to various modifications and alternative forms, specifics thereof have been shown by way of example in the drawings and will be described in detail below. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION OF THE PREFERRED EMBODIMENT

In the following description of the illustrated embodiments, references are made to the accompanying drawings, which form a part hereof, and in which is shown by way of illustration various embodiments in which the invention may be practiced. It is to be understood that other embodiments may be utilized, and structural and functional changes may be made without departing from the scope of the present invention.

In an ultrasonic device running at resonance in longitudinal mode, the longitudinal ultrasonic motion, d, behaves as a simple sinusoid at the resonant frequency as given by:

$$d = A \sin$$

where:

ω=the radian frequency which equals times the cyclic frequency, f; t is time; and A=the zero-to-peak amplitude.

The longitudinal excursion is defined as the peak-to-peak (p-t-p) amplitude, which is just twice the amplitude of the sine wave or 2A.

Referring now to FIG. 1, a perspective view of an ultrasonic shear system 100 is illustrated in accordance with embodiments of the present invention. FIG. 1 illustrates an ultrasonic shear system 100 including an ultrasonic signal generator 150, an ultrasonic transducer 180, a switch 120, and an ultrasonic shear 130 in accordance with the present invention. Ultrasonic shear 130 may be used, for example, for open or laparoscopic surgery, or for other non-medical cutting applications such as the cutting of textiles, confectionary, or other cutting. The ultrasonic transducer 180 is also known as a "Langevin stack." The ultrasonic transducer 180 may be an integral number of one-half system wavelengths (nλ/2) in length as will be described in more detail later.

The ultrasonic transducer 180 may be piezoelectric or magnetostrictive. The ultrasonic transducer 180 may be electrically coupled to ultrasonic signal generator 150 using a cable 170. The switch 120 may be a foot activated switch, a hand activated switch, a voice activated switch, or use other switching and activation technologies. The switch 120 may be coupled to the generator 150 via a cable 175, or may alternately use the cable 170 if the switch is located in or on the ultrasonic shear 130.

Figure 2:
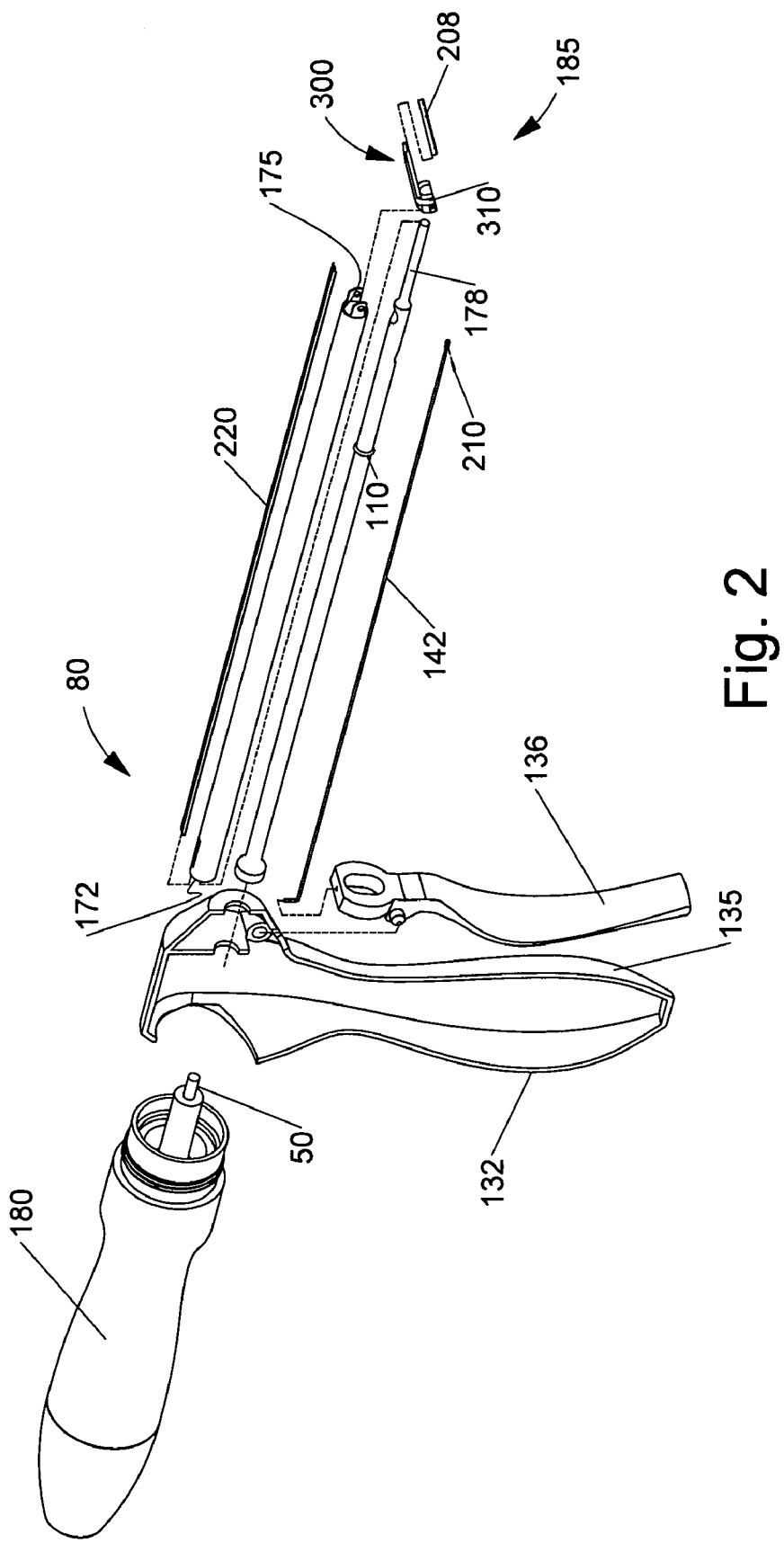
FIG. 2 is an exploded view of an ultrasonic shear device in accordance with embodiments of the present invention.

FIG. 2 is an exploded view of the ultrasonic shear 130 in accordance with embodiments of the present invention. The ultrasonic shear 130 may be attached to and removed from the ultrasonic transducer 180 as a unit. The proximal end of the ultrasonic shear 130 preferably acoustically couples to the distal end of the ultrasonic transducer 180 as shown in FIG. 1. It will be recognized that the ultrasonic shear 130 may be coupled to the acoustic assembly 80 by any suitable means.

The ultrasonic shear 130 may include an instrument housing 135, shown in section in FIG. 2, an elongated support member 172, and an end-effector 185. The end-effector 185 may include a clamp arm assembly 300 and a cutting blade 178. The clamp arm assembly 300 includes, for example, a clamp 310 and a pad 208. The clamp arm assembly 300 may be coupled to the reciprocal member 142 using, for example, a pin 210. The instrument housing 135 includes a pivoting handle 136, and a fixed handle 132, configured as a portion of the housing 135 and configured to facilitate actuation of the ultrasonic shear 130. The instrument housing 135, pivoting handle 136, and fixed handle 132, are preferably fabricated from polycarbonate. It is contemplated that these components may be made from any suitable material.

Ultrasonic transducer 180 may be considered part of an acoustic assembly 80 that includes a waveguide 179 and a cutting blade 178. The ultrasonic transducer 180 converts the electrical signal from ultrasonic signal generator 150 into mechanical energy that results in primarily longitudinal vibratory motion of the ultrasonic transducer 180 and the waveguide 179. A suitable generator, model GEN01 for example, is available from Ethicon Endo-Surgery, Inc., Cincinnati, Ohio. When the acoustic assembly 80 is energized, a vibratory motion standing wave is generated through the acoustic assembly 80. The amplitude of the vibratory motion at any point along the acoustic assembly 80 depends on the location along the acoustic assembly 80 at which the vibratory motion is measured. A minimum or zero crossing in the vibratory motion standing wave is generally referred to as a node (i.e., where motion is usually minimal), and an absolute value maximum or peak in the standing wave is generally referred to as an anti-node. The distance between an anti-node and its nearest node is one-quarter wavelength (λ/4).

In order for the acoustic assembly 80 to deliver energy, all components of acoustic assembly 80 must be acoustically coupled. The distal end of the ultrasonic transducer 180 may be acoustically coupled to the proximal end of an ultrasonic waveguide 179 by a threaded connection such as a stud 50.

The components of the acoustic assembly 80 are preferably acoustically tuned such that the length of the acoustic assembly 80 is an integral number of one-half wavelengths (nλ/2), where the wavelength λ is the wavelength of a pre-selected or operating longitudinal vibration drive frequency fd of the acoustic assembly 80, and where n is any positive integer.

The ultrasonic waveguide 179 extends through an aperture 175 of the elongated support member 172. The ultrasonic waveguide 179 may be substantially semi-flexible. It will be recognized that the ultrasonic waveguide 179 may be substantially rigid or may be, for example, a flexible wire. Ultrasonic vibrations are transmitted along the ultrasonic waveguide 179 in a longitudinal direction to vibrate the ultrasonic cutting blade 178 as will be described in more detail below.

The ultrasonic waveguide 179 may, for example, have a length substantially equal to an integral number of one-half system wavelengths (n$\lambda$/2). The ultrasonic waveguide 179 may be fabricated from a solid core shaft constructed out of material that propagates ultrasonic energy efficiently, such as titanium alloy (i.e., Ti-6Al-4V) or an aluminum alloy. It is contemplated that the ultrasonic waveguide 179 may be fabricated from any other suitable material. The ultrasonic waveguide 179 may also amplify the mechanical vibrations transmitted to the ultrasonic cutting blade 178 as is well known in the art.

It will be recognized that the ultrasonic waveguide 179 may have any suitable cross-sectional dimension. For example, the ultrasonic waveguide 179 may have a substantially uniform cross-section or the ultrasonic waveguide 179 may be tapered at various sections or may be tapered along its entire length or include any suitable horn configuration.

The ultrasonic waveguide 179 may also amplify the mechanical vibrations transmitted through the ultrasonic waveguide 179 to the ultrasonic cutting blade 178 as is well known in the art. The ultrasonic waveguide 179 may further have features to control the gain of the longitudinal vibration along the ultrasonic waveguide 179 and features to tune the ultrasonic waveguide 179 to the resonant frequency of the system.

The ultrasonic cutting blade 178 may have a length substantially equal to one-quarter of a system wavelength ($\lambda$/4) or less. The distal end of ultrasonic cutting blade 178 may be disposed near an antinode in order to provide the maximum excursion of the ultrasonic cutting blade 178. When the transducer assembly is energized, the distal end of the ultrasonic cutting blade 178 is configured to move in the range of, for example, from about 10 to about 500 microns peak-to-peak, and preferably in the range of about 30 to about 150 microns at a predetermined vibrational frequency and having predefined ranges of motion.

The ultrasonic cutting blade 178 may be made from a solid core shaft constructed of material which propagates ultrasonic energy, such as a titanium alloy (i.e., Ti-6Al-4V) or an aluminum alloy. It will be recognized that the ultrasonic cutting blade 178 may be fabricated from any other suitable material. It is also contemplated that the ultrasonic cutting blade 178 may have a surface treatment to improve the delivery of energy and desired tissue effect. For example, the ultrasonic cutting blade 178 may be micro-finished, coated, plated, etched, grit-blasted, roughened or scored to enhance coagulation and cutting of tissue and/or reduce adherence of tissue and blood to the end-effector and/or provide visual indications of damage or wear. Additionally, the ultrasonic cutting blade 178 may be sharpened or shaped to enhance its characteristics.

As illustrated in FIG. 2, the ultrasonic waveguide 179 may include one or more stabilizing silicone rings 110 (one being shown) positioned at various locations around the periphery of the ultrasonic waveguide 179. The rings 110 may dampen undesirable vibration and isolate the ultrasonic energy from the elongated support member 172 assuring the flow of ultrasonic energy in a longitudinal direction to the ultrasonic cutting blade 178 with maximum efficiency. The rings 110 may be secured to the ultrasonic waveguide 179 by injection molding, a ring-groove, or other locating method.

In one embodiment, during use of the ultrasonic shear 130, when the pivoting handle 136 is moved toward the fixed handle 132, the pivoting handle 136 may drive a reciprocal member 142 distally to pivot a clamp arm assembly 300 into a closed position. The movement of the pivoting handle 136 in the opposite direction may drive the reciprocal member 142 in the opposite direction, for example, proximally, thereby pivoting the clamp arm assembly 300 into its open position. The pivoting handle 136 may, for example, be moved manually by an operator, be configured for attachment to a robotic manipulation system, and/or may be spring biased in one or both directions.

Figure 3:
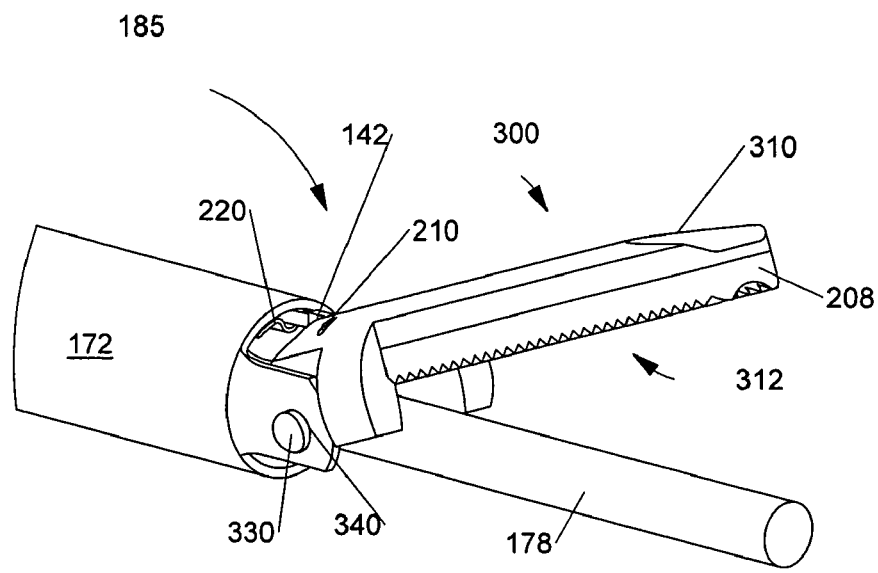
FIG. 3 is a magnified perspective view of the end-effector of the device illustrated in FIG. 2 in accordance with embodiments of the present invention.

FIG. 3 depicts embodiment of a magnified perspective view of the end-effector 185 in accordance with the present invention. The clamp arm assembly 300 may include tissue pad 208 attached thereto for squeezing tissue between the ultrasonic cutting blade 178 and clamp arm assembly 300. The clamp arm assembly, in one embodiment, includes a clamp arm 310 and a tissue pad 208, which may be formed, for example, of a polymeric or other compliant material, for engaging the ultrasonic cutting blade 178 when the clamp arm assembly 300 is in the closed position. Preferably, the tissue pad 208 is formed of a material having a low coefficient of friction but which has substantial rigidity to provide tissue-grasping capability, such as, for example, TEFLON, a trademark name of E.I. Du Pont de Nemours and Company for the polymer polytetraflouroethylene (PTFE). The tissue pad 208 may be mounted to the clamp arm 310 by an adhesive, by a mechanical fastening assembly, or by other suitable fastening method.

Serrations 312 may be formed in the clamping surfaces of the tissue pad 208 and may extend perpendicular to the axis of the ultrasonic cutting blade 178 to allow tissue to be grasped, manipulated, coagulated and cut without slipping between the clamp arm assembly 300 and ultrasonic cutting blade 178. The clamp arm assembly 300 may be coupled to elongated support member 172 using a barrel 330 that is insertable into an opening 340 of elongated support member 172.

Figure 4:
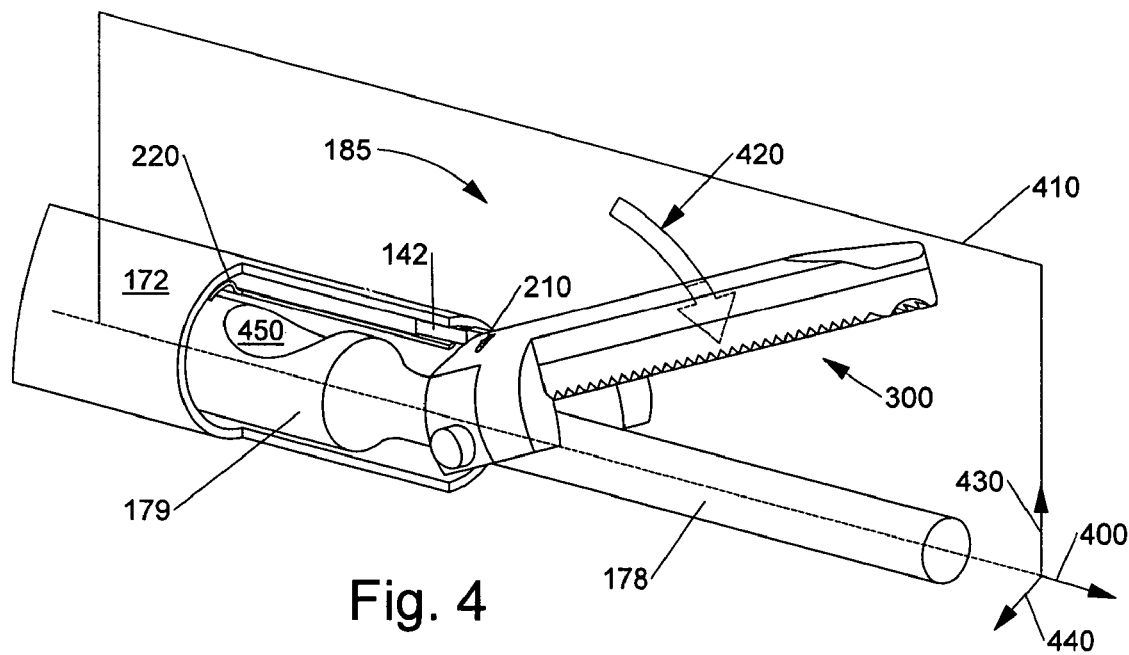
FIG. 4 is a magnified perspective cutaway view of an embodiment of an end-effector of a device in accordance with the present invention.

FIG. 4 is a magnified perspective cutaway view of an embodiment of end-effector 185 in accordance with the present invention. In one embodiment, illustrated in FIG. 4, the reciprocal member 142 may be operatively connected to the clamp arm assembly 300 using pin 210. End-effector 185 may extend distally from elongated support member 172 and may include cutting blade 178 coupled to ultrasonic waveguide 179, wherein longitudinal axis 400 extends through the center of mass of cutting blade 178. Clamp arm assembly 300 is, in one embodiment, configured for an opposable movement 420 with respect to the cutting blade 178 to cut material between the cutting blade 178 and the clamp arm assembly 300 using ultrasonic motion of the cutting blade 178. The opposable movement 420 defines a vertical plane 410. Vertical plane 410 has a vertical axis 430 orthogonal to both the longitudinal axis 400 and a horizontal axis 440. In one embodiment, clamp arm assembly 300 is operatively connected to the reciprocal member 142 so that reciprocal movement of the reciprocal member 142 clamps the clamp arm assembly 300 with respect to the cutting blade 178. The proximal end of the cutting blade 178 may include asymmetry 450 configured to convert longitudinal motion of the waveguide into motion of the cutting blade in both the longitudinal axis 400 and vertical axis 430 directions concurrently.

Figure 5A:
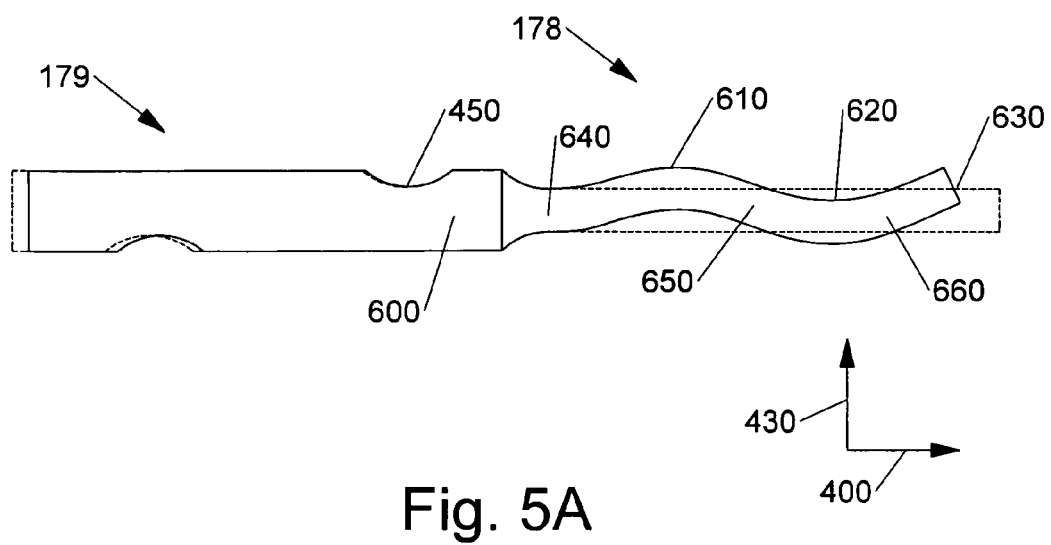
FIG. 5A is a magnified plan view of a waveguide and cutting blade in accordance the embodiments of the present invention illustrated in FIG. 4, where the cutting blade is illustrated at an exaggerated excursion in a compression phase of ultrasonic motion.
Figure 5B:
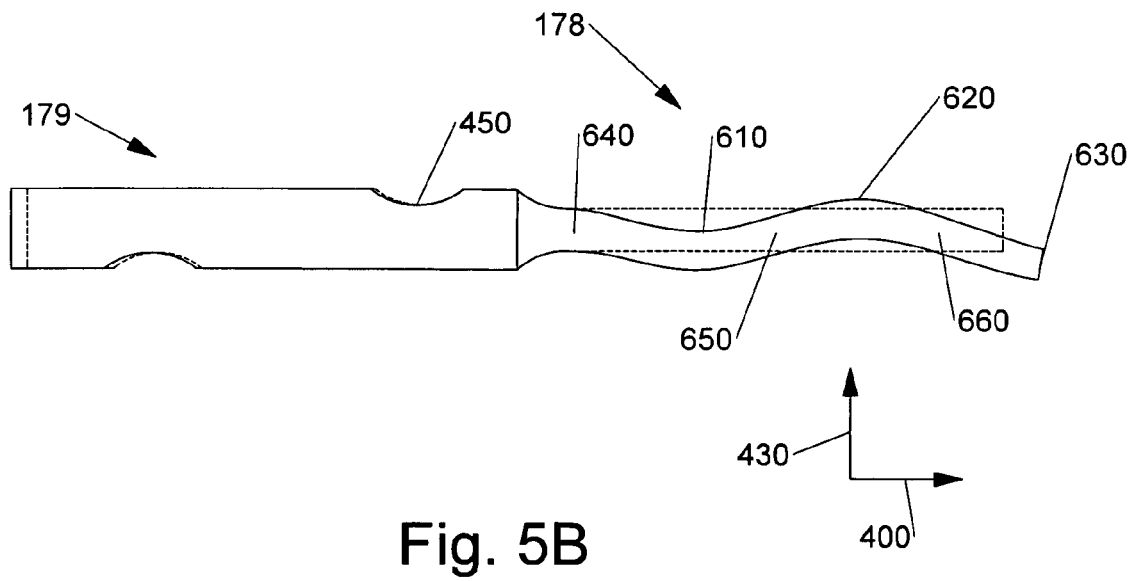
FIG. 5B, is a magnified plan view of a waveguide and cutting blade of FIG. 5A, where the cutting blade is illustrated at an exaggerated excursion in an expansion phase of ultrasonic motion.

FIG. 5A is a magnified plan view of the waveguide 179 and cutting blade 178 of the type illustrated in FIG. 4, where the cutting blade 178 is illustrated at an exaggerated excursion in a compression phase of ultrasonic motion. FIG. 5B is a magnified plan view of waveguide 179 and cutting blade 178 of FIG. 5A, where cutting blade 178 is illustrated at an exaggerated excursion in an expansion phase of ultrasonic motion. The ultrasonic motion of the cutting blade 178 is seen in FIGS. 5A and 5B to have concurrent y-direction motion and x-direction motion. The x-direction motion (Longitudinal axis) in the waveguide 179 and cutting blade 178 may have a node 600 and an anti-node 630. The concurrent y-direction motion (vertical axis) may have nodes 640, 650 and 660, and anti-nodes 610, 620, and 630. The concurrent motion may provide advantages, such as providing a longer active length of the cutting blade 178, which may improve the blade's effectiveness.

Embodiments of devices in accordance with the present invention provide an excursion of the cutting blade 178 in the direction of the horizontal axis that is limited to less than about 92%. Other embodiments of devices in accordance with the present invention provide for an excursion of the cutting blade 178 in the direction of the vertical axis 430 of more than about 8% of an excursion of the cutting blade 178 in the direction of the longitudinal axis 400. Embodiments of devices in accordance with the present invention provide an excursion of the cutting blade 178 in the direction of the horizontal axis 440 that is more than 8% of an excursion of the cutting blade in the direction of the longitudinal axis 400. Still further embodiments of devices in accordance with the present invention provide an excursion of the cutting blade 178 in the direction of the vertical axis 430 and the horizontal axis 440 of more than 8% of an excursion of the cutting blade 178 in the direction of the longitudinal axis 400. These excursions are examples only, and any excursion in contemplated to be within the scope of the present invention. For example, it may be useful to provide an ultrasonic shear 130 having a vertical axis 430 direction excursion at 50% or more of the longitudinal axis 400 direction excursion. It is contemplated that greater than 85% of the excursion in the longitudinal axis 400 direction of the waveguide 179 may be converted to vertical axis 430 direction excursion and/or horizontal axis 440 direction excursion of the cutting blade 178 in accordance with embodiments of the present invention.

Figure 6:
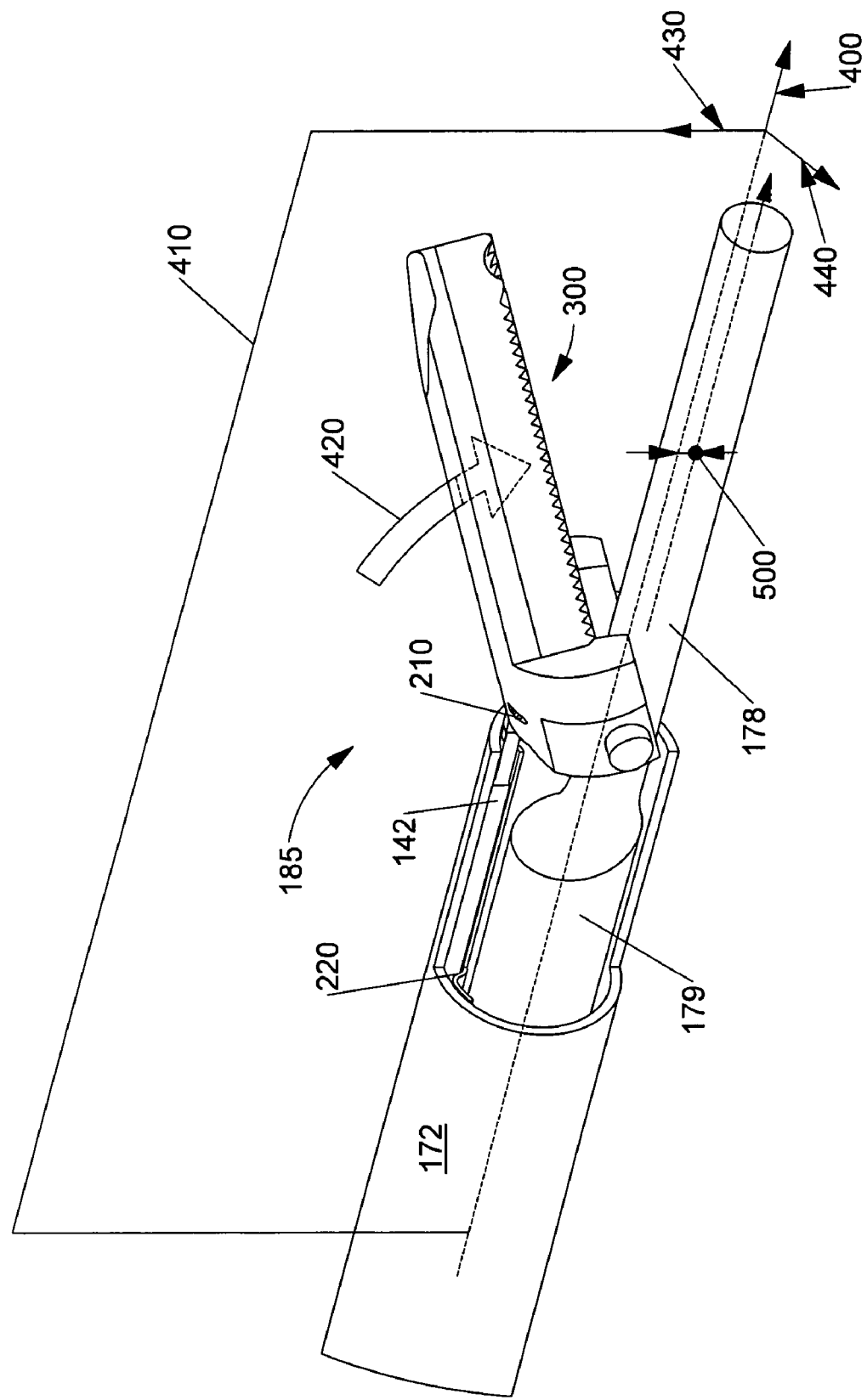
FIG. 6 is a magnified perspective cutaway view of another embodiment of an end-effector of a device in accordance with the present invention.

FIG. 6 is a magnified perspective cutaway view of another embodiment of the end-effector 185 in accordance with the present invention. The embodiment of the end-effector 185 illustrated in FIG. 6 differs from the embodiment of the end-effector 185 illustrated in FIG. 4 by the positioning of the cutting blade 178 relative to the waveguide 179. The ultrasonic shear 130 illustrated in FIG. 6 provides the desired vertical plane motion of the cutting blade 178, similarly to the embodiment illustrated in FIG. 4, without requiring the asymmetry 450 seen in FIG. 4. The cutting blade 178 illustrated in FIG. 6 has a center of mass 500 of the cutting blade 178 offset from the longitudinal axis 400, which converts longitudinal motion of the waveguide 179 into motion of the cutting blade 178 in both the longitudinal axis 400 and vertical axis 430 directions concurrently. Although the asymmetry 450 (FIG. 4) is not necessary in the arrangement of the cutting blade 178 illustrated in FIG. 6, an asymmetry may be added to provide more complex motion of the cutting blade 178, such as in all three axis directions concurrently.

Figure 7A:
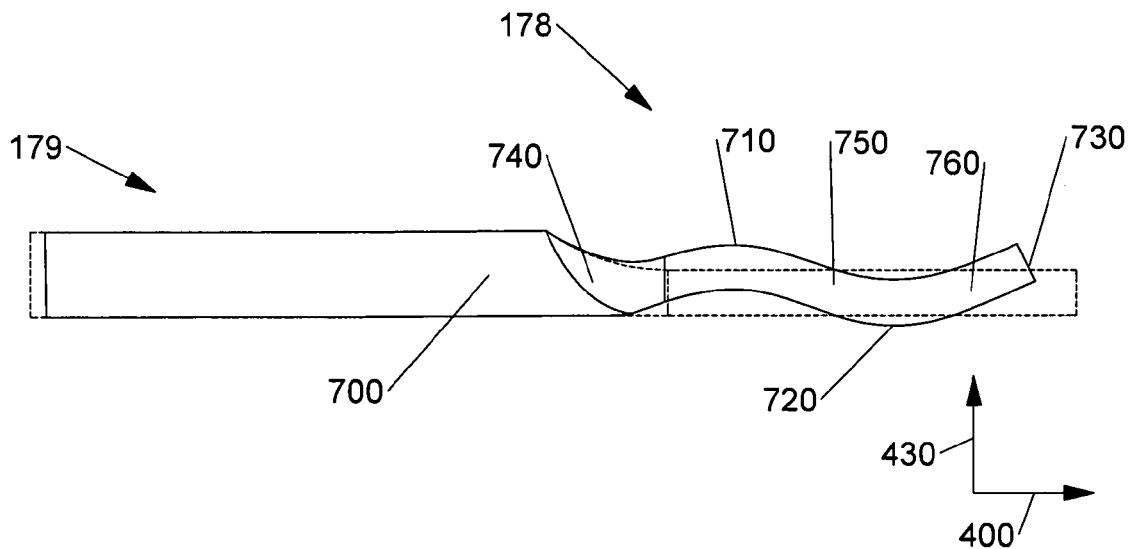
FIG. 7A is a magnified plan view of the waveguide and cutting blade in accordance with embodiments of the present invention illustrated in FIG. 6, where the cutting blade is illustrated at an exaggerated excursion in a compression phase of ultrasonic motion.
Figure 7B:
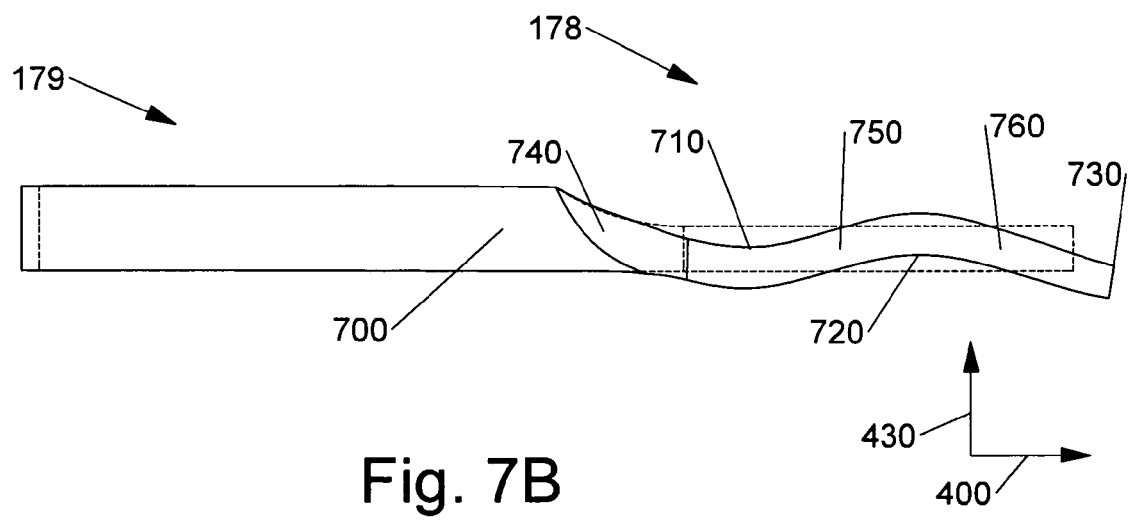
FIG. 7B is a magnified plan view of the waveguide and cutting blade of FIG. 7A, where the cutting blade is illustrated at an exaggerated excursion in an expansion phase of ultrasonic motion.

FIG. 7A is a magnified plan view of a waveguide 179 and cutting blade 178 such as is illustrated in FIG. 6, where the cutting blade 178 is illustrated at an exaggerated excursion in a compression phase of ultrasonic motion. FIG. 7B is a magnified plan view of the waveguide 179 and cutting blade 178 of FIG. 7A, where the cutting blade 178 is illustrated at an exaggerated excursion in an expansion phase of ultrasonic motion. The ultrasonic motion of the cutting blade 178 is seen in FIGS. 7A and 7B to have concurrent y-direction motion and x-direction motion. The x-direction motion (longitudinal axis 400) in the waveguide 179 and cutting blade 178 may have a node 700 and an anti-node 730. The concurrent y-direction motion (vertical axis 430) may have nodes 740, 750 and 760, and anti-nodes 710, 720, and 730.

Straight symmetric ultrasonic blades in general have tip excursions that lie along the longitudinal axis, which may also be designated the x-axis. A normalized y-direction excursion percentage (% y) in a clamping instrument at the end-effector 185 is calculated by taking the magnitude of the excursion in the direction normal to the longitudinal axis and in the vertical plane, and dividing that magnitude by the magnitude of the maximum longitudinal excursion, and then multiplying the dividend by one hundred. A primary vibration excursion is the magnitude of the major axis of the ellipse or ellipsoid created by a point on the ultrasonic cutting blade 178 when the ultrasonic cutting blade 178 is activated. The measurement of excursions is more fully explained in IEC international standard 61847, titled Measurement and Declaration of the Basic Output Characteristics of ultrasonic surgical systems. A normalized excursion percentage (% x, % y, % z) in ultrasonic cutting blade 178 or ultrasonic waveguide 179 is calculated by taking the magnitude of a secondary vibration excursion, and dividing that magnitude by the magnitude of the primary tip vibration excursion, and then multiplying the dividend by one hundred. Secondary tip vibration excursion is the magnitude of a minor axis, or other arbitrary axis, of the ellipse or ellipsoid created by a point on the ultrasonic cutting blade 178 when the ultrasonic cutting blade 178 is activated. Typically vibration excursions and excursion percentages are calculated from anti-nodal excursions, where maximum excursions are established.

Figure 8:
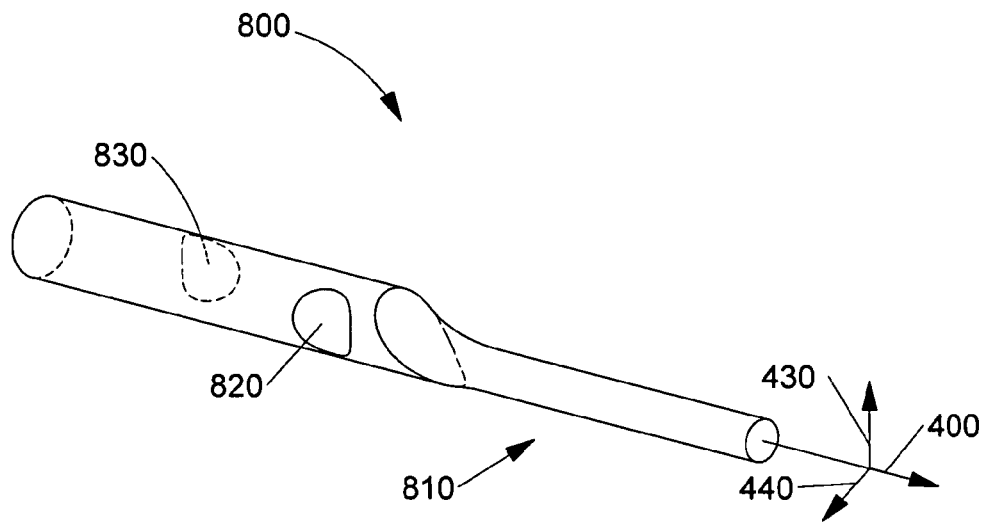
FIG. 8 is a magnified perspective view of an embodiment of a cutting blade in accordance with the present invention.

FIG. 8 is a magnified perspective view of an embodiment of a cutting blade 800 in accordance with the present invention. The cutting blade 800 illustrates an offset blade 810 in combination with one or more asymmetries 820, 830, providing a more complex motion than available with only an offset blade. For two or more asymmetries 820, 830, the asymmetries 820, 830 may be spaced along and around the cutting blade 800 to provide the desired cutting blade 800 motion. For example, the asymmetry 820 is illustrated 180 degrees around the cutting blade 800 from the asymmetry 830.

Figure 9:
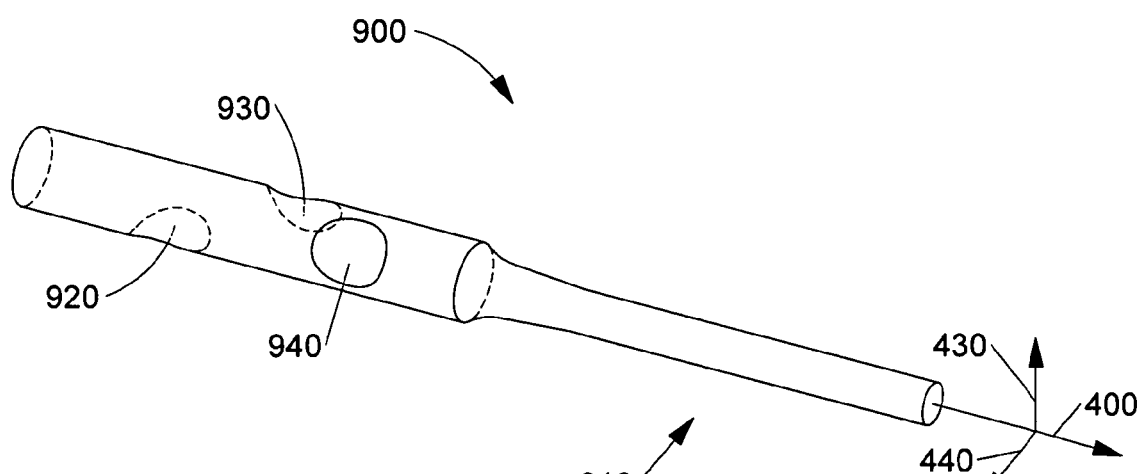
FIG. 9 is a magnified perspective view of an embodiment of a cutting blade in accordance with the present invention.

FIG. 9 is a magnified perspective view of an embodiment of a cutting blade 900 in accordance with the present invention. The cutting blade 900 illustrates a blade 910 in combination with three or more asymmetries 920, 930, 940 providing a more complex motion than available with less asymmetries. For three or more asymmetries 920, 930, 940, the asymmetries 920, 930, 940 may be spaced along and around the cutting blade 900 to provide the desired cutting blade 900 motion. For example, the asymmetry 920 is illustrated 120 degrees around the cutting blade 900 from the asymmetry 930 and the asymmetry 940.

Figure 10:
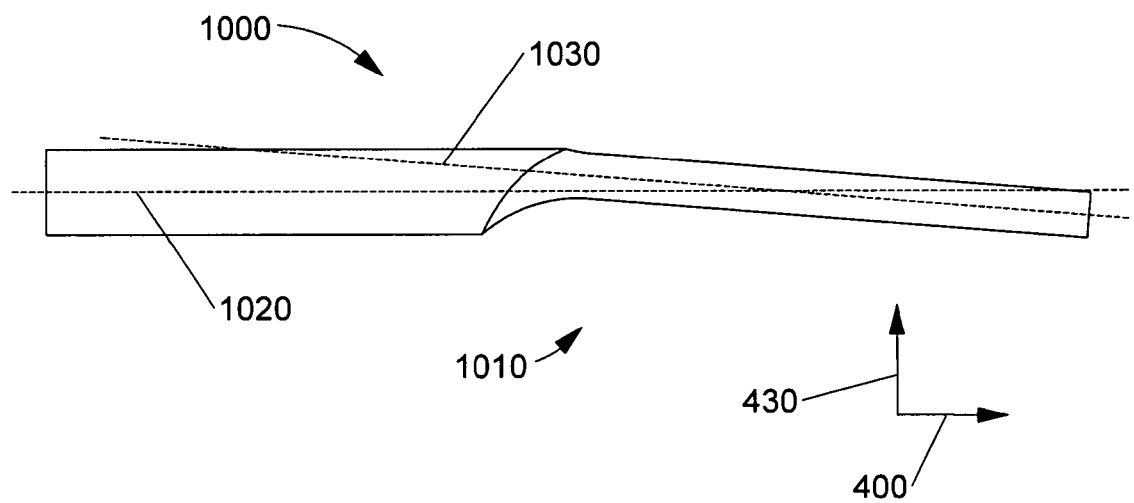
FIG. 10 is a magnified perspective view of an embodiment of a cutting blade in accordance with the present invention.

FIG. 10 is a magnified perspective view of an embodiment of a cutting blade 1000 in accordance with the present invention. The cutting blade 1000 has a longitudinal axis 1020 and a blade axis 1030, where the axes are not parallel. The blade 1000 illustrated in FIG. 10 may have an angled blade 1010 center of mass that lies on the longitudinal axis, but due to the angled blade 1010 combined angle and offset from the centerline of the cutting blade 1000, the angled blade 1010 may still exhibit the desired motion similar to other blades in accordance with the present invention.

Each feature disclosed in this specification (including any accompanying claims, abstract, and drawings), may be replaced by alternative features having the same, equivalent or similar purpose, unless expressly stated otherwise. Thus, unless expressly stated otherwise, each feature disclosed is one example only of a generic series of equivalent or similar features.

While embodiments of the present invention have been shown and described herein, it will be obvious to those skilled in the art that such embodiments are provided as examples only. Numerous variations, changes, and substitutions will be apparent to those skilled in the art without departing from the invention. Accordingly, it is intended that the invention be limited only by the scope of the appended claims.

What is claimed is:

1. An ultrasonic clamping device, comprising:
   a housing;
   an elongated support member having a proximal end coupled to the housing, and a distal end, the elongated support member defining a longitudinal axis;
   an ultrasonic waveguide positioned within the elongated support member, wherein the longitudinal axis extends through the center of mass of the ultrasonic waveguide;
   an actuating assembly coupled to the housing, the actuating assembly comprising:
   an actuator; and
   a reciprocal member operatively connected to the actuator; and
   an end-effector extending distally from the distal end of the elongated support member, the end-effector comprising:
   a cutting blade configured to cut using ultrasonic motion, the cutting blade coupled to the ultrasonic waveguide, wherein the center of mass of the cutting blade is offset along an axis parallel to and offset from the longitudinal axis, thereby providing motion of the cutting blade in both the longitudinal and vertical axes concurrently without producing significant vertical axis motion in the waveguide; and
   a clamp arm coupled to the distal end of the elongated support member and configured for opposable movement with respect to the cutting blade, the opposable movement defining a vertical plane, the vertical plane having a vertical axis orthogonal to both the longitudinal axis and a horizontal axis, the clamp arm operatively connected to the reciprocal member so that reciprocal movement of the reciprocal member opposes the clamp arm with the cutting blade.

2. The ultrasonic clamping device of claim 1, wherein an excursion of the cutting blade in the direction of the horizontal axis is limited to less than about 92%.

3. The ultrasonic clamping device of claim 1, wherein an excursion of the cutting blade in the direction of the vertical axis is more than about 8% of an excursion of the cutting blade in the direction of the longitudinal axis.

4. The ultrasonic clamping device of claim 1, wherein an excursion of the cutting blade in the direction of the horizontal axis is more than about 8% of an excursion of the cutting blade in the direction of the longitudinal axis.

5. The ultrasonic clamping device of claim 1, wherein an excursion of the cutting blade in the direction of the vertical axis and the horizontal axis is more than about 8% of an excursion of the cutting blade in the direction of the longitudinal axis.

6. The ultrasonic device of claim 1, wherein the ultrasonic clamping device is sterilized.

7. An ultrasonic clamping device, comprising:
   a housing;
   an ultrasonic waveguide coupled to the housing, the ultrasonic waveguide comprising a longitudinal axis extending through the center of mass of the ultrasonic waveguide;
   an actuating assembly coupled to the housing, the actuating assembly comprising:
   an actuator; and
   a reciprocal member operatively connected to the actuator; and
   an end-effector extending distally from the housing, the end-effector comprising:
   a cutting blade coupled to the ultrasonic waveguide, wherein the longitudinal axis extends through the center of mass of the cutting blade; and
   a clamp arm configured for opposable movement with respect to the cutting blade to cut material between the cutting blade and the clamp arm using ultrasonic motion, the opposable movement defining a vertical plane, the vertical plane having a vertical axis orthogonal to both the longitudinal axis and a horizontal axis, the clamp arm operatively connected to the reciprocal member so that reciprocal movement of the reciprocal member clamps the clamp arm with respect to the cutting blade;
   wherein the proximal end of the cutting blade comprises an asymmetry configured to convert longitudinal motion of the waveguide into motion of the cutting blade in both the longitudinal and vertical axis directions concurrently.

8. The ultrasonic clamping device of claim 7, wherein an excursion of the cutting blade in the direction of the horizontal axis is limited to less than about 92%.

9. The ultrasonic clamping device of claim 7, wherein an excursion of the cutting blade in the direction of the vertical axis is more than about 8% of an excursion of the cutting blade in the direction of the longitudinal axis.

10. The ultrasonic clamping device of claim 7, wherein an excursion of the cutting blade in the direction of the horizontal axis is more than about 8% of an excursion of the cutting blade in the direction of the longitudinal axis.

11. The ultrasonic clamping device of claim 7, wherein an excursion of the cutting blade in the direction of the vertical axis and the horizontal axis is more than about 8% of an excursion of the cutting blade in the direction of the longitudinal axis.

12. The ultrasonic clamping device of claim 7, wherein the cutting blade is symmetrical with respect to the vertical plane.

13. The ultrasonic device of claim 7, wherein the cutting blade is circularly symmetric about a blade axis extending through the center of mass of the cutting blade.

14. The ultrasonic device of claim 7, wherein the cutting blade is circularly symmetric about a blade axis extending through the center of mass of the cutting blade, wherein the blade axis is parallel to the longitudinal axis.

15. The ultrasonic device of claim 7, wherein the ultrasonic device is sterilized.

16. An ultrasonic device, comprising:
   an ultrasonic waveguide comprising a longitudinal axis extending through the center of mass of the ultrasonic waveguide; and
   a cutting blade configured to cut using ultrasonic motion, the cutting blade coupled to the ultrasonic waveguide, wherein the longitudinal axis extends through the center of mass of the cutting blade, the proximal end of the cutting blade comprising an asymmetry configured to convert longitudinal motion of the waveguide into motion of the cutting blade in both the longitudinal and vertical axis directions concurrently, thereby converting at least a portion of the longitudinal motion of the ultrasonic waveguide into motion of the cutting blade normal to the longitudinal axis.

17. The ultrasonic device of claim 16, wherein an excursion of the cutting blade in the direction of the longitudinal axis is limited to less than about 92%.

18. The ultrasonic device of claim 16, wherein an excursion of the cutting blade in the direction of the vertical axis is more than about 8% of an excursion of the cutting blade in the direction of the longitudinal axis.

19. The ultrasonic device of claim 16, wherein an excursion of the cutting blade in the direction of the vertical axis is more than about 8% of an excursion of the cutting blade in the direction of the longitudinal axis.

20. The ultrasonic device of claim 16, wherein the ultrasonic device is sterilized.

* * * * *